United States Patent [19]

Trantzas et al.

[11] Patent Number: 5,952,585
[45] Date of Patent: Sep. 14, 1999

[54] PORTABLE PRESSURE SENSING APPARATUS FOR MEASURING DYNAMIC GAIT ANALYSIS AND METHOD OF MANUFACTURE

[75] Inventors: Constantin M. Trantzas, Briarcliff Manor, N.Y.; Douglas D. Haas, Jr., Sparta, N.J.

[73] Assignee: CIR Systems, Inc., N.J.

[21] Appl. No.: 08/871,265

[22] Filed: Jun. 9, 1997

[51] Int. Cl.$^6$ .................................................. G01D 7/00
[52] U.S. Cl. ..................................................... 73/862.046
[58] Field of Search ........................ 338/47; 73/862.046, 73/862.381, 862.68

[56] References Cited

U.S. PATENT DOCUMENTS

| | | | |
|---|---|---|---|
| 3,174,125 | 3/1965 | Curby | 338/47 |
| 3,806,471 | 4/1974 | Mitchell | 252/518 |
| 3,987,259 | 10/1976 | Larson | 200/5 |
| 4,127,752 | 11/1978 | Lowthrop | 200/5 |
| 4,136,682 | 1/1979 | Pedotti | 128/2 |
| 4,195,643 | 4/1980 | Pratt, Jr. | 128/779 |
| 4,246,452 | 1/1981 | Chandler | 200/5 |
| 4,257,305 | 3/1981 | Friend et al. | 84/1.24 |
| 4,267,728 | 5/1981 | Manley et al. | 73/172 |
| 4,426,884 | 1/1984 | Polchaninoff | 73/172 |
| 4,489,302 | 12/1984 | Eventoff | 338/99 |
| 4,492,949 | 1/1985 | Peterson et al. | 73/862.046 |
| 4,503,705 | 3/1985 | Polchaninoff | 73/172 |
| 4,555,954 | 12/1985 | KIm | 73/862.046 |
| 4,734,034 | 3/1988 | Maness et al. | 433/68 |
| 4,813,436 | 3/1989 | Jan Au | 128/779 |
| 4,856,993 | 8/1989 | Maness et al. | 433/68 |
| 5,033,291 | 7/1991 | Podoloff et al. | 73/172 |
| 5,086,652 | 2/1992 | Kropp | 73/767 |
| 5,253,656 | 10/1993 | Rincoe et al. | 128/782 |
| 5,296,837 | 3/1994 | Yaniger | 338/470.32 |
| 5,361,133 | 11/1994 | Brown et al. | 356/376 |
| 5,431,064 | 7/1995 | Franz | 73/862.68 |
| 5,474,087 | 12/1995 | Nashner | 128/782 |
| 5,541,570 | 7/1996 | McDowell | 338/47 |
| 5,563,354 | 10/1996 | Kropp | 73/862.381 |

FOREIGN PATENT DOCUMENTS

| | | | |
|---|---|---|---|
| 56-186391 | 11/1981 | Japan | G06K 11/06 |
| 2193040 | 1/1988 | United Kingdom | G08C 21/00 |

OTHER PUBLICATIONS

Craik, R.L. Oatis, C.A., *Gait Analysis: Theory and Application*, "Foot Fall Measurement Technology" Chapter 12.

Primary Examiner—Richard Chilcot
Assistant Examiner—Jewel V. Thompson
Attorney, Agent, or Firm—Sofer & Haroun, LLP

[57] ABSTRACT

A pressure sensing array for measuring forces applied thereto and particularly for measuring the gait of a person. The pressure sensing array includes a first plurality of current driven electrodes attached to and supported by a thin, flexible backing sheet and a second plurality of current sensing electrodes disposed in an insulating arrangement positioned on the first plurality of current sensing electrodes. A third plurality of bridge electrodes are also provided so as to connect the current driven electrodes and the current sensing electrodes such that upon sensing a pressure on opposite ends of one of said bridge electrodes, an electrical conduction is provided between the current driven electrodes and the current sensing electrodes. A method of manufacturing the apparatus is also disclosed.

26 Claims, 13 Drawing Sheets

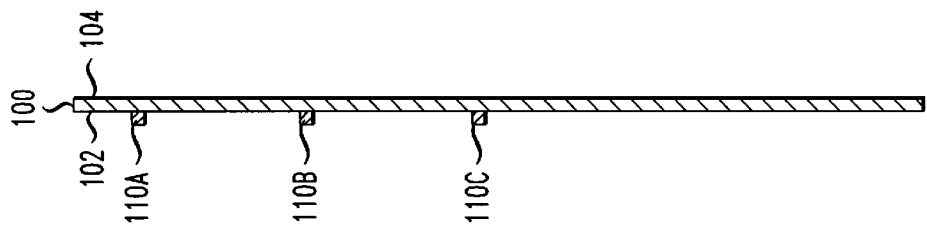
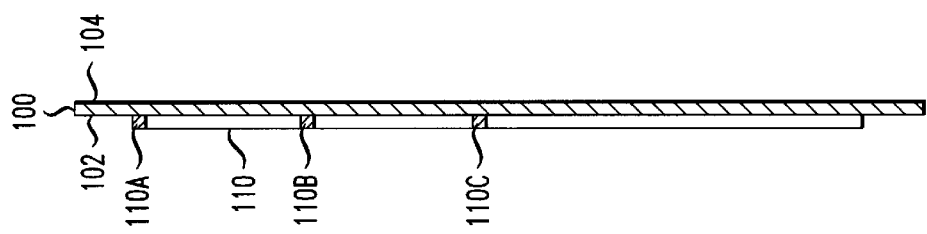
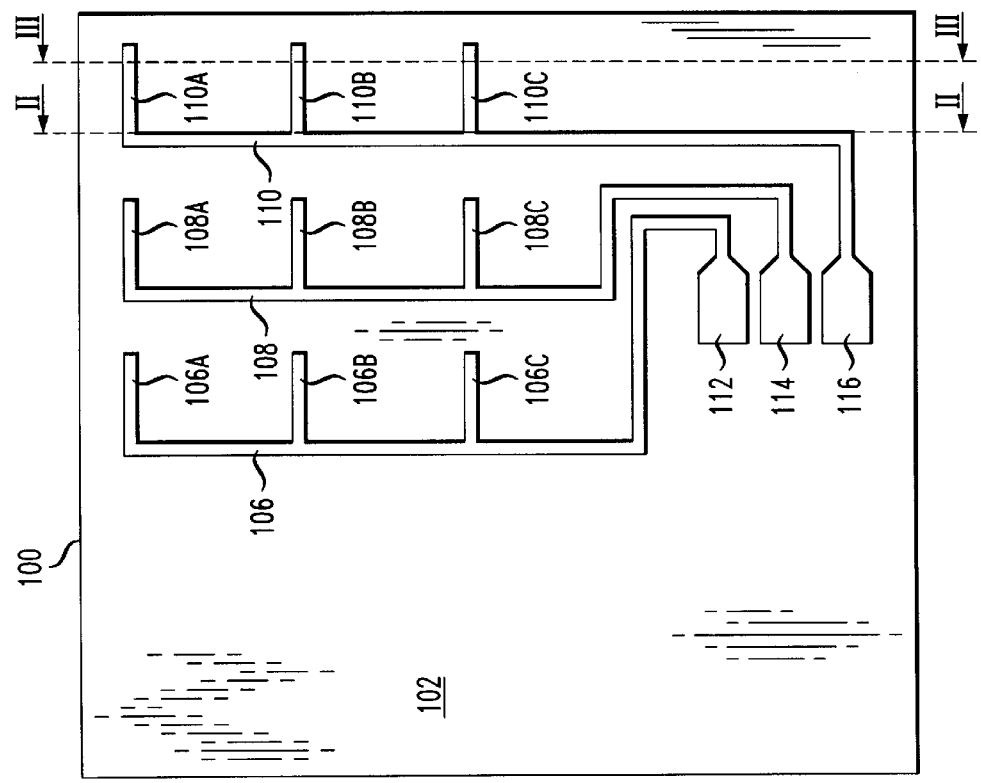

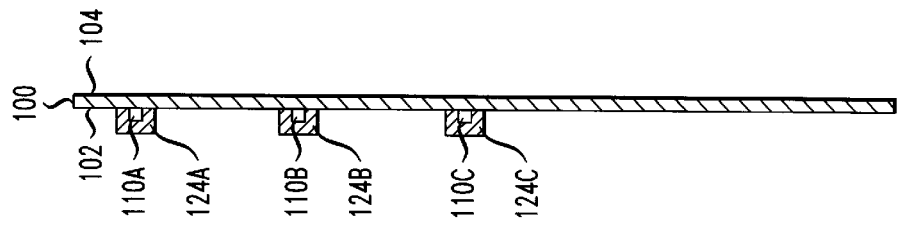
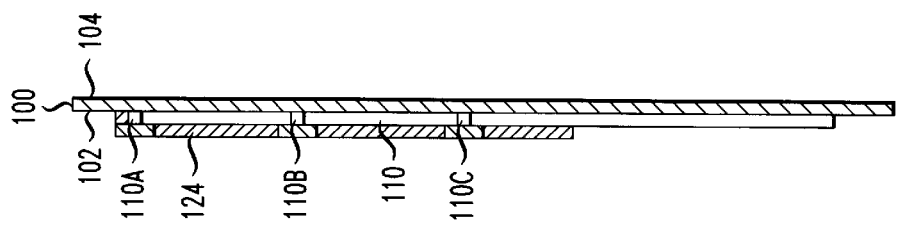
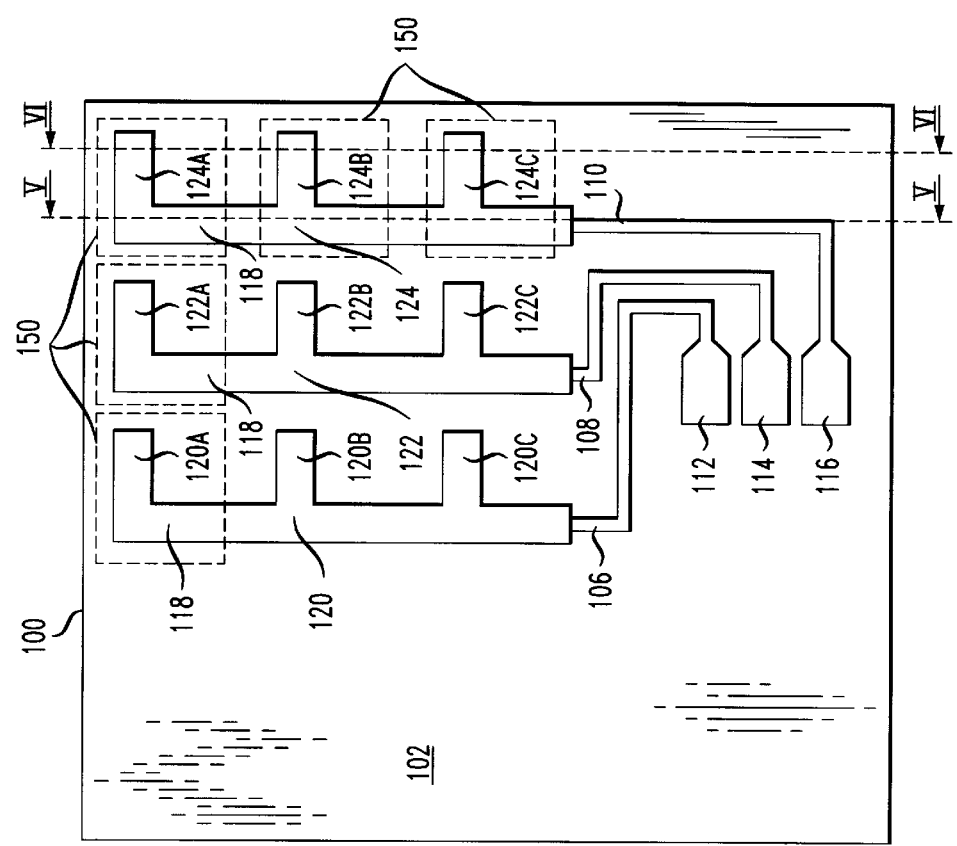

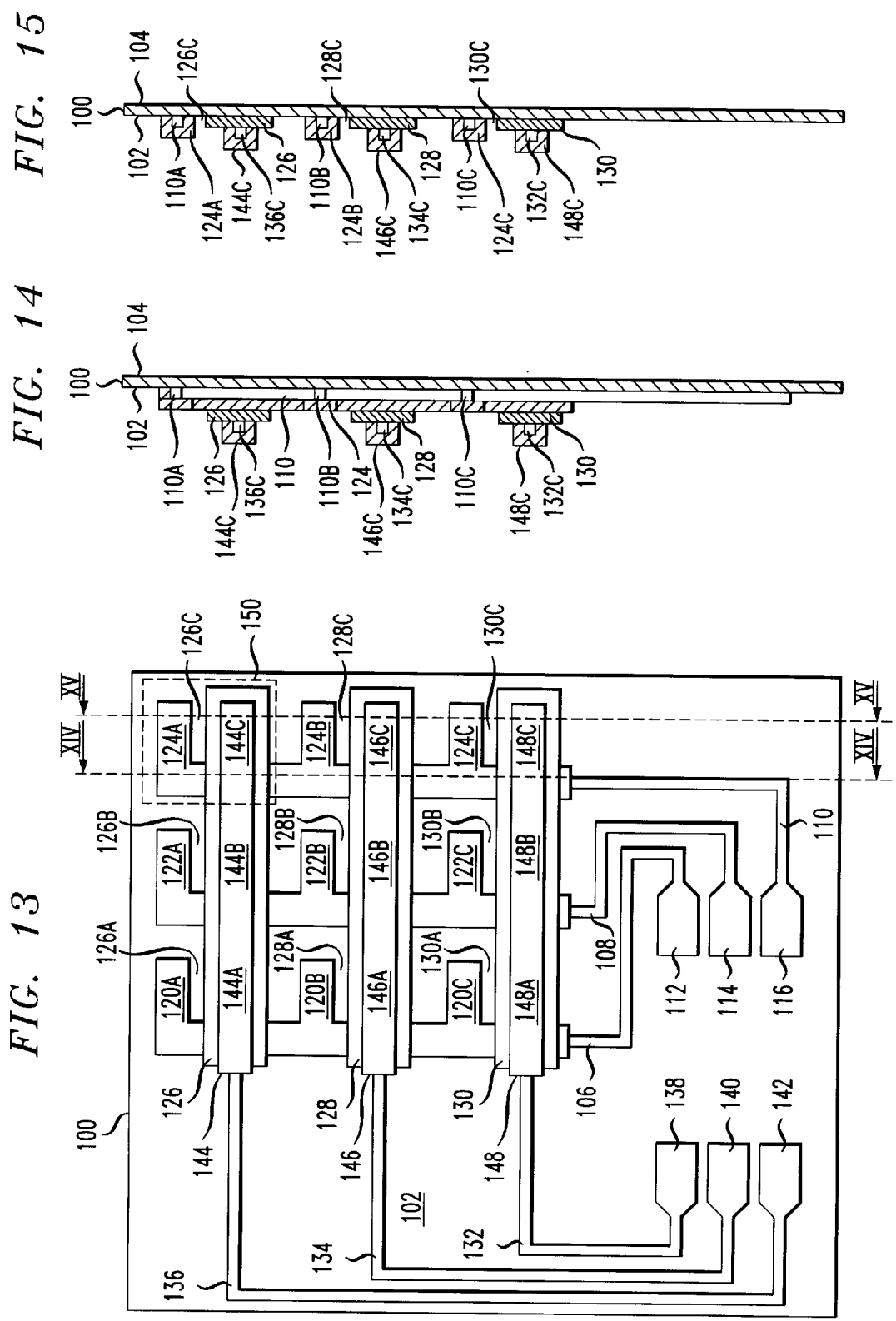

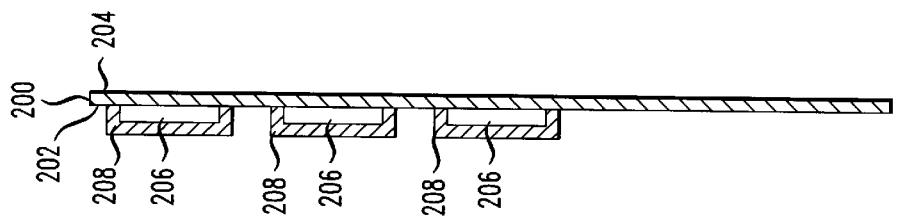
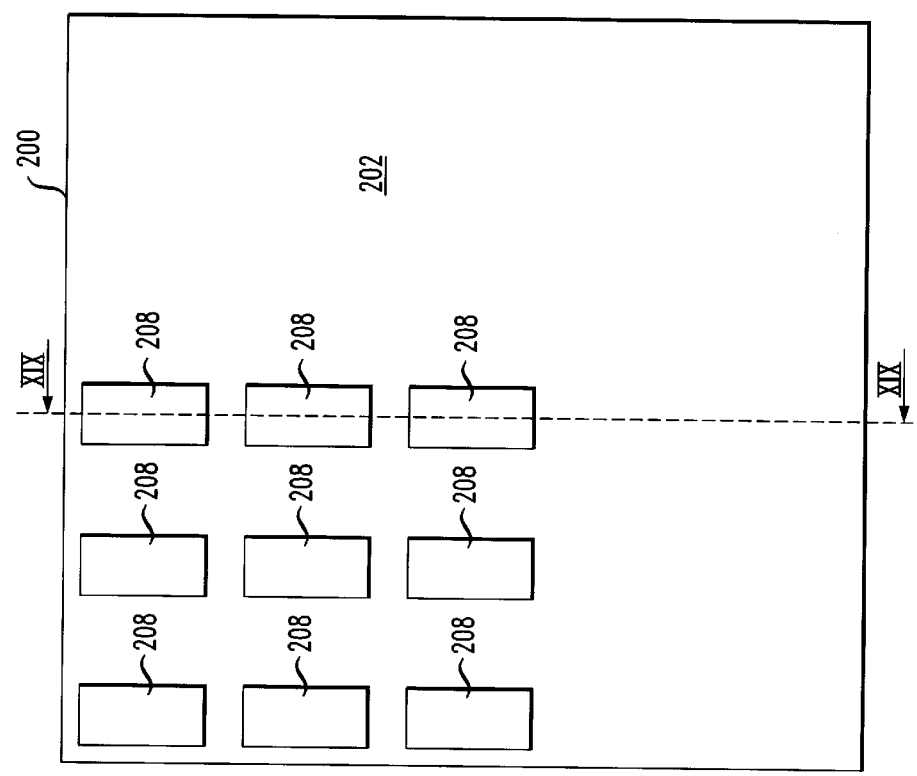

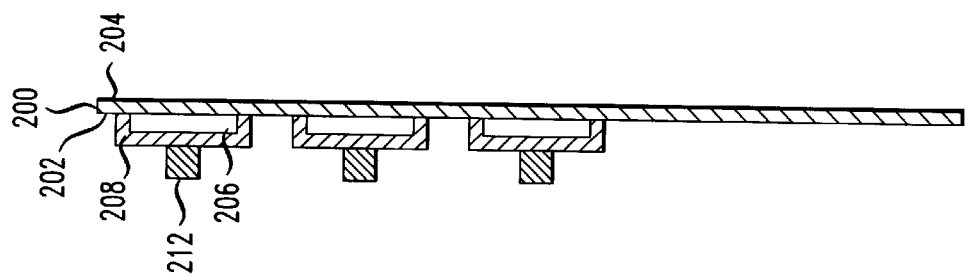
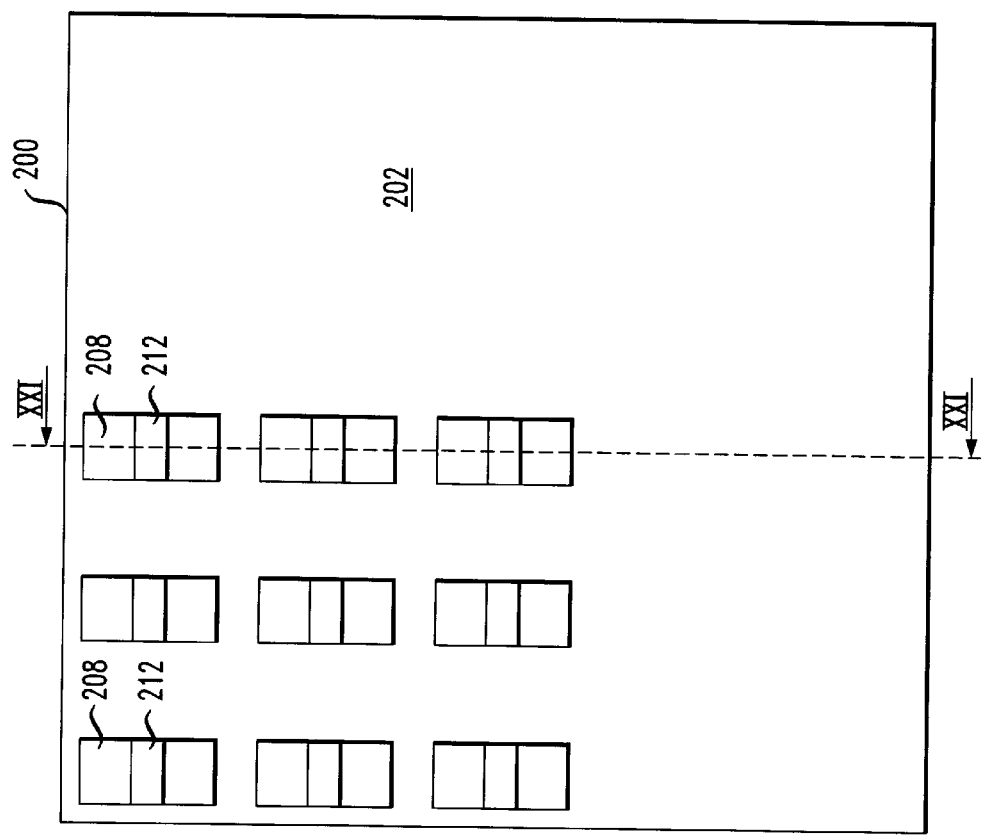

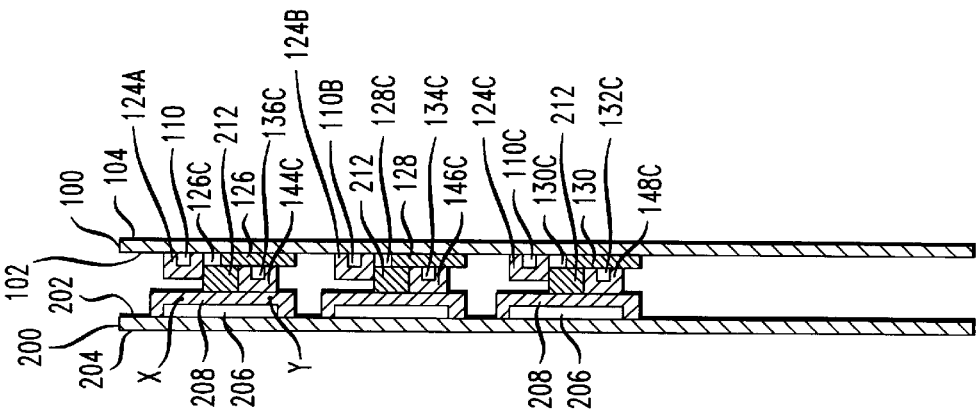
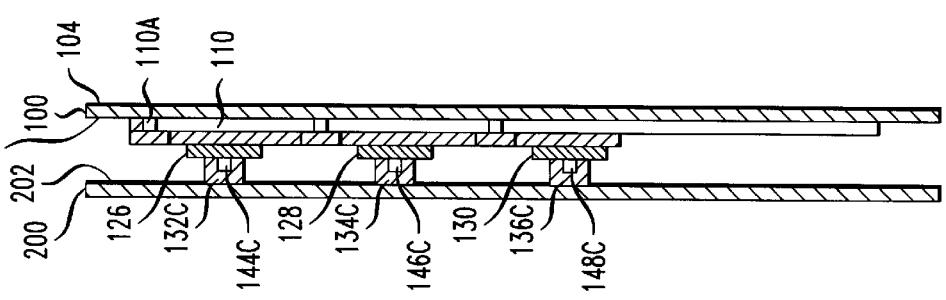
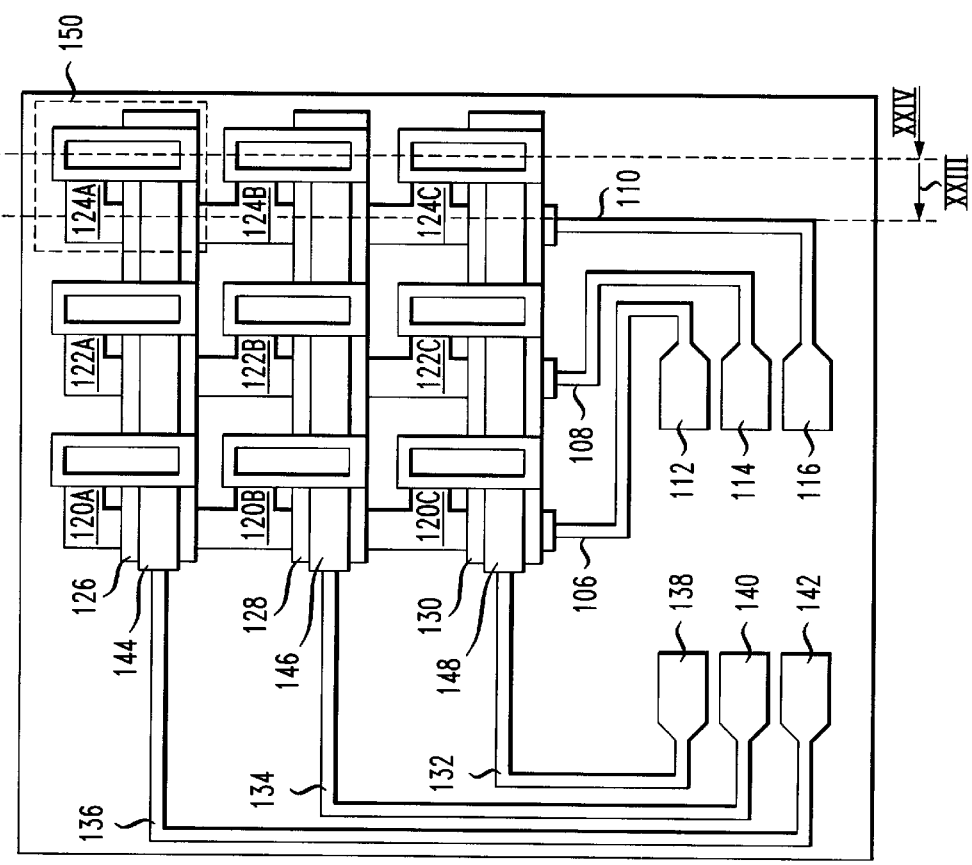

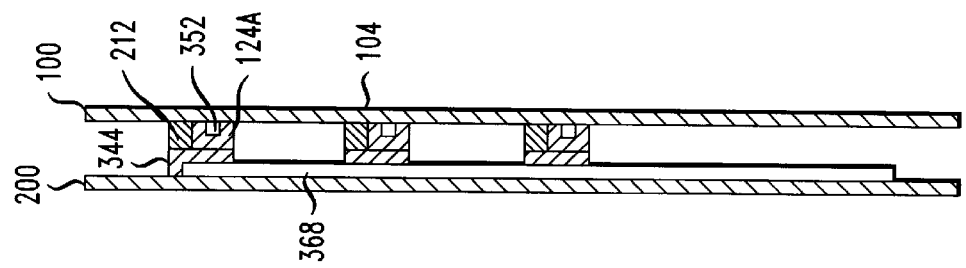
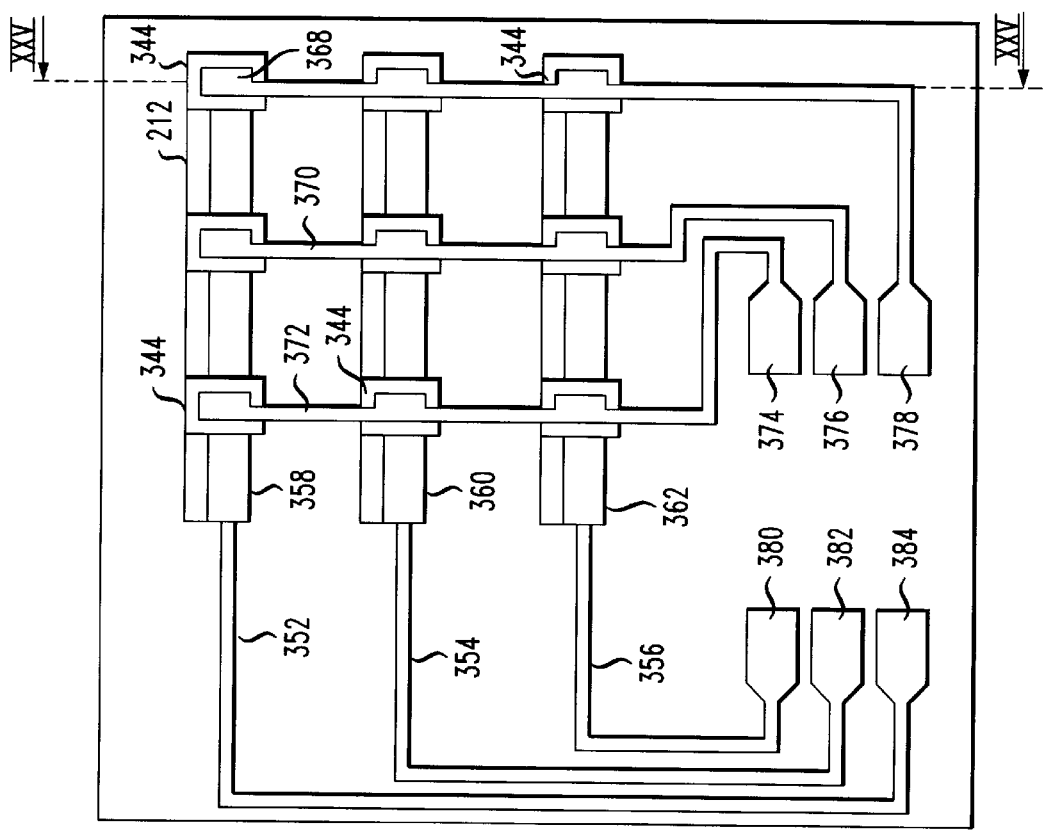

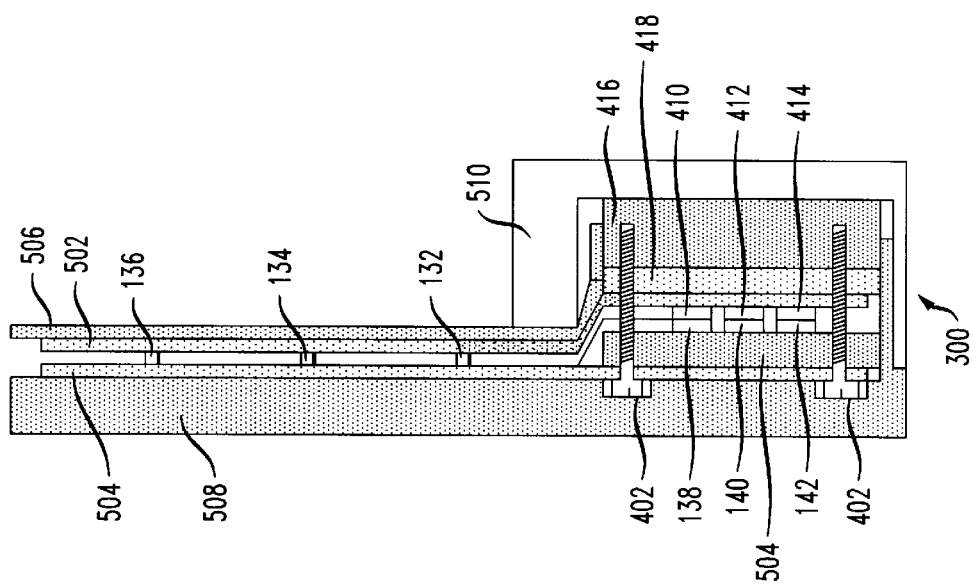
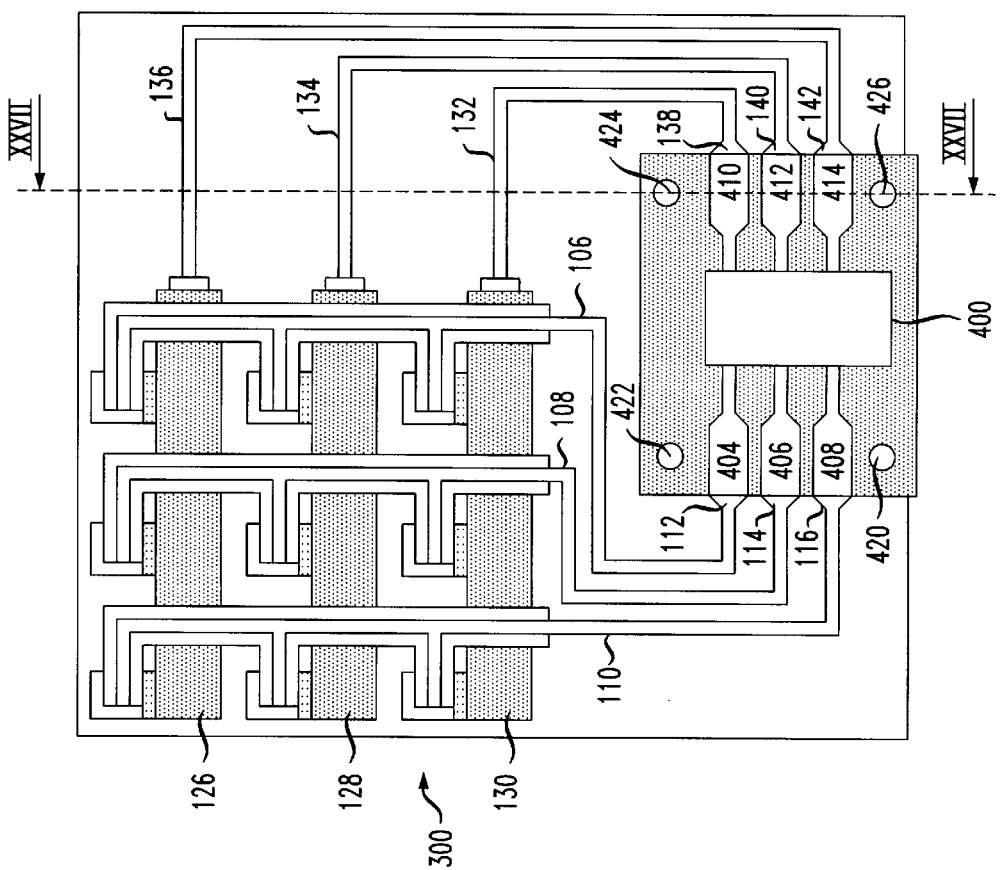

PORTABLE PRESSURE SENSING APPARATUS FOR MEASURING DYNAMIC GAIT ANALYSIS AND METHOD OF MANUFACTURE

FIELD OF THE INVENTION

This invention relates to a portable walkway for the measuring and analyzing the gait of a living being, and more particularly to a portable walkway for the capture of footprint profiles during the gait of a patient, the walkway having the ability to record the pressure, spatial and temporal parameters of events taking place during the gait.

BACKGROUND OF THE INVENTION

It is known that rehabilitation and physical therapy is a major contributor of treatment in order to restore the physical mobility and functionality of patients with injuries affecting ambulation. It is also known that during the course of such treatments an objective evaluation coupled with the medical practitioner's subjective evaluation can change the results and course of treatment dramatically. Such objective evaluation may be obtained by employing a gait analysis system. Typically, the movements of a patient undergoing a physical therapy regiment is periodically measured by a gait analyzer. However, previous studies have revealed that the test/retest repeatability of prior art gait analyzers are unreliable. As physicians and care providers increasingly demand justification for the quality and type of treatment given to patient, the effectiveness and reliability of equipment is of ever-increasing importance.

Some of the prior art gait analyzers employ pressure sensors to measure a change in pressure by converting a change in resistance using a plurality of transducers arranged in a row/column array fashion and where each transducer can be uniquely addressed by the electronic control signals.

U.S. Pat. No. 5,033,29 to Podoloff et al. discloses a flexible tactile sensor for measuring foot pressure distributions. Podoloff teaches a force and pressure sensor provided with two sets of parallel electrodes positioned facing one another and arranged so that electrodes of one set cross the electrodes of the second set to create a plurality of electrode intersections. Between the electrodes at each intersection lie an adhesive layer for securing the first and second electrodes in facing relationship. The adhesive layer is of an adjustable thickness which serves to permit preloading or to provide a variable threshold level for the sensor. Use of this sensor may, however, provide discomfort to the user since it must be inserted within the user's shoe or some other orthotic device in order to measure the force between the wearer's foot and the supporting surface beneath the foot.

The force and/or pressure transducer arrays disclosed in U.S. Pat. No 5,253,656, U.S. Pat. No. 5,033,291 and U.S. Pat. No. 4,734,034 are designed to identify forces exerted between a body part and an external surface and are not suitable for the objects of this invention. The transducer arrays as disclosed in these prior art references utilizes adhesive as a separator between top and bottom layers upon which the arrays are disposed. When a load is applied to a sensor, a minimum load is required in order to compress the adhesive so as to bring the top and bottom layers into contact. This minimum load depends on the thickness and resilience of the adhesive and the thickness of the flexible backing material from which the top and bottom layers are fabricated. Further increases on the load changes the resistance between the top and bottom layers in some linear or exponential fashion. Upon removal of the load, the adhesive separator is responsible for breaking the contact between the top and bottom layers. The time required to accomplish this depends on the characteristics of the adhesive and the thickness of the flexible backing materials of the top and bottom layers. These variables affect the linearity of the sensor. Additionally, changes in the thickness and resilience of the adhesive separator result over the passage of time, as a result of environmental conditions, the frequency of use and the size of the load applied. These conditions render the transducer arrays disclosed in these references as single-use sensors.

The amount of time required to overcome the adhesive response and break the contact between the top and bottom layers is the "turn-off delay". In the prior art devices disclosed in U.S. Pat. No. 5,253,656, U.S. Pat. No. 5,033, 291 and U.S. Pat. No. 4,734,034, the turn-off delay is very high and produces extensive hysteresis which, in turn, effects the turn-off linearity of the sensor on the array. In order to minimize hysteresis, the separation time of the adhesive separator must be increased. These prior art references accomplish this by utilizing very thin top and bottom flexible layers of backing material. The use of thin layers of backing material produces multiple adverse side effects, such as deformation of sensing area when rolled, and reduction of the minimum load required to first compress the adhesive separator and commence sensor activity. Reduction of the minimum load is undesirable because it makes it easier for a load to trigger neighboring sensors.

These prior art references also assume that the load surface are in contact with the sensor is equal or greater than the active area of the sensor. When the load surface area becomes smaller than the sensor active area, the results are rendered invalid because the determination of whether the actual load changed or the load surface area changed cannot be made.

Other instruments have been explored for dynamic gait analysis. U.S. Pat. No. 4600, 016 to Boyd et al. describes elongated platform upon which the subject may stride and a moveable camera disposed below the platform for viewing the plantar aspects of the subject's foot. The camera which is mounted on a trolley driven by a cable and pulley is connected to a belt worn by the subject so that the camera is moved synchronously with the subject ambulating on the platform. A fluorescent light is placed on one edge of the platform; the remaining edges being covered with reflective material to minimize loss of light. The surface of the platform is heated to minimize loss of light. The surface is heated to minimize condensation. However, this instrument is not portable and it does not measure the relative forces of the plantar aspects of the foot. It is obvious that by attaching a cable to move the camera below will alter the natural gait of the subject. Also, lights under the surface of a transparent platform will increase the field of depth and this alters the natural gait.

U.S. Pat. No. 4,136,682 to Pedotti and U.S. Pat. No. 4,195,643 to Pratt disclose apparatuses and methods for evaluating locomotive functionality which comprise rigid platforms with force and/or pressure transducing members. Such methods including methods utilizing cinematography instruments are not suitable to accurately identify the geometry and geometrical outline of the footfalls and are not suitable for portability especially for use in evaluating home care patients.

The present invention employs an apparatus and a method of manufacturing said apparatus which is directed to measuring the pressure, spatial and temporal parameters of events taking place during the gait of a patient so that the outcome of treatment may be assessed. Such measurements enable health care providers to document the provided benefits and the degree of benefit provided. The present invention not only addresses the problems associated with the accuracy and linearity of the transducer, but also with the problems associated with the minimum scan time of the array, which is the time required to sample each and every transducer of the array at least once. The present invention also addresses the problems associated with the turn-on hysteresis when a load is applied, the turn-off hysteresis when a load is removed, the miss-triggering of the pressure transducers located in close vicinity to the load, and the location and method of interconnection to the electronic controls such as to produce a portable long walkway that can be rolled onto a drum for storage and relocation.

OBJECTS AND SUMMARY OF THE INVENTION

It is the object of the present invention to provide a transducer array which overcomes the problems associated with prior art.

It is another object to provide such array which is very thin and does not require appreciable motion to actuate it.

It is an additional object to provide such array comprised of a plurality of pressure transducers, closely spaced and specifically designed to avoid triggering of neighboring transducers.

It is an additional object to incorporate such transducer arrays between two layers of flexible synthetic material to produce a long walkway.

It is a further object to provide such walkway to capture and identify the geometry of the footprints as a function of time as a living being ambulates across its top surface.

It is still an additional object to provide such walkway to capture the relative arrangement of the footprints as a function of time.

Yet another object is to provide such walkway to capture the relative strength of pressure exerted by the foot as a function of time and as a function of the relative arrangement of the footprints.

Yet another object is to provide information not only to the force exerted by the foot, but also the locations where the force is exerted and the position of such locations in relation to one another within the footprint or related footprints and as a function of time.

Yet another object is to provide such walkway utilized by all ambulating patients, including those carrying assistive devices and ambulatory aids, such as crutches, canes, walkers, etc.

Yet another object is to provide such walkway that can be utilized with subjects that can ambulate across the walkway with or without shoes.

Yet another object is to provide such walkway thin enough not to alter the subject's natural gait pattern at the beginning or the end of the gait test and without requiring an initial acceleration area or a final deceleration area.

Yet another object is to provide such walkway that can be rolled on a tube with a specific outer diameter that would not destroy or alter the walkway construction and specifications.

Yet another object is to provide such walkway that can be laid over any flat surface, such as carpet, wood, tiles etc. without distorting the measurements.

Yet another object is to provide such walkway that protects the electronics from the electrostatic discharge produced as the subject ambulates across the top surface.

Yet another object is to provide such walkway with continuous top and bottom surfaces.

Yet another object is to provide such walkway with top and bottom surfaces which cannot be harmed by the use of common liquids used to clean, disinfect and sanitize the walkway.

Yet another object is to provide a portable walkway that can be removed and carried to a different location with very little effort.

Yet another object is to provide a walkway that requires minimum setup and test time and that does not require the placement of any devices on the body of the person.

Yet another object is to provide a walkway which is economical.

Yet another object of the present invention is to incorporate the measurements derived from the gait analysis into a scoring method and provide the score as the consistent medical standard for the level of disability.

Yet another object is to provide government institutions and private care providers with objective information to distinguish between voluntary and involuntary ambulation disability of a patient when applying for long term disability insurance.

Yet another object of the present invention is to provide practitioners in the medical field with objective information of the dynamic parameters measured during the gait of a patient.

Yet another object of the present invention is to provide physicians and therapists with the statistics from these measurements during the course of treatment to monitor, catalog, and standardize the relation between diagnosis, treatment and outcome.

Yet another object of the present invention is to provide physicians and therapists the ability to tailor therapy by diagnosis, change therapy during the course of treatment or stop therapy according to the measurable objective outcome of the present invention.

Yet another object is to document the course of treatment and provide progress reports to management, insurance providers and referring physicians.

Yet another object is to evaluate patients and prescribe the appropriate orthotic devices for patients with podiatric problems, orthotic devices, knee and hip implant surgery, and amputees, as well as to evaluate devices prescribed to minimize the difference in length between the left and right legs.

These and other objects of the invention are realized by providing an apparatus and method of manufacturing an apparatus for recording and measuring the distance, time and pressure of footprint events occurring during the dynamic gait of a person utilizing the apparatus. The apparatus comprises a portable electronic walkway that employs a plurality of pressure transducer arrays. Each pressure transducer array employs a plurality of pressure transducers with sufficient density to detect the profile of a footprint as the person ambulates across the top surface. The pressure transducers of each array are arranged in specific patterns with properties to allow roll-up of the electronic walkway and to avoid miss-triggering of neighboring transducers. Preferably, the pressure transducers of each array include a plurality of electrodes attached to and supported by a thin flexible backing sheet to provide a set of current driven electrodes. A second plurality of electrodes are disposed in an insulating arrangement on said first electrodes to provide a set of current sensing electrodes. A third plurality of bridge electrodes are arranged between said first and second electrodes, such that a resistive layer separates the bridge electrodes from the first and second electrodes. Upon sensing a pressure on opposite end portions of the bridge electrode, an electrical conduction is provided between the first driven electrodes and the second sensing electrodes.

The above description sets forth rather broadly the more important features of the present invention in order that the detailed description thereof that follows may be understood, and in order that the present contributions to the art may be better appreciated. Other objects and features of the present invention will become apparent from the following detailed description considered in conjunction with the accompanying drawings. It is to be understood, however, that the drawings are designed solely for the purposes of illustration and not as a definition of the limits of the invention, for which reference should be made to the appended claims.

DETAILED DESCRIPTION OF THE DRAWINGS

In the drawings in which like reference characters denote similar elements throughout the several views.

FIG. 1 illustrates a plan view of a portion of a first flexible material layer and having traces of a conductive material silk screened on an inner side to form the primary conductive traces according to one embodiment of the present invention;

FIGS. 2 and 3 illustrate cross sections of the first flexible material layer of FIG. 1 viewed along lines II—II and III—III respectively, of FIG. 1;

FIG. 4 illustrates a plan view of a portion of a first flexible material layer as illustrated in FIG. 1 according to one embodiment of the present invention and including a continuous thin layer of pressure responsive resistive material which covers the primary conductive traces;

FIGS. 5 and 6 illustrate cross sections of the first flexible material layer of FIG. 4 viewed along lines V—V and VI—VI, respectively of FIG. 4;

FIG. 13 illustrates a plan view of a portion of a first flexible material layer as illustrated in FIG. 10 according to one embodiment of the present invention and having a continuous thin layer of pressure responsive resistive material disposed upon each secondary conductive trace to form secondary resistive traces;

FIGS. 14 and 15 illustrate cross sections of the first flexible material layer of FIG. 13 viewed along lines XIV—XIV and XV—XV respectively, of FIG. 13.

FIG. 18 illustrates a plan view of a portion of a second flexible material layer as illustrated in FIG. 16 according to one embodiment of the present invention wherein each conductive rocking bridge surface is fully covered with a thin layer of pressure responsive resistive material to form pressure resistive rocking bridges;

FIG. 19 illustrates a cross section of the second flexible material of FIG. 18 viewed along line XIX—XIX of FIG. 18;

FIG. 20 illustrates a plan view of a portion of a second flexible material layer as illustrated in FIG. 18 according to one embodiment of the present invention wherein a thick adhesive material is silk-screened across each pressure resistive rocking bridge to form a rocker;

FIG. 21 illustrates a cross section of the second flexible material layer 200 viewed along line XXI—XXI of FIG. 20;

FIG. 22 illustrates a plan view of a portion of a first and second flexible material layers overlaid upon each other to create a sensor array according to one embodiment of the present invention;

FIGS. 23 and 24 illustrate a cross sections of the overlaid first and second flexible material layers viewed along lines XXIII—XXIII and XXIV—XXIV respectively, of FIG. 22;

FIG. 25 illustrates a plan view a plan view of a portion of a first and second flexible material layers overlaid upon each other to create a sensor array according to an alternative embodiment of the present invention;

FIG. 25a illustrates a cross section of the overlaid first and second flexible material layers viewed along lines XXV—XXV respectively, of FIG. 25;

FIG. 27 is a plan view of the sensor array of FIG. 22 according to one embodiment of the present invention and having a circuit board connected to the sensor array;

FIG. 28 is a cross section of the sensor array and circuit board of FIG. 27 viewed long line XXVII—XXVII of FIG. 27;

DETAILED DESCRIPTION OF THE PRESENTLY PREFERRED EMBODIMENT

Figure 8:
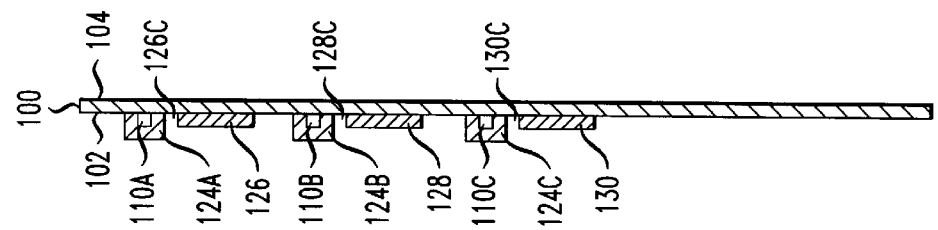
FIGS. 8 and 9 illustrate cross sections of the first flexible material layer of FIG. 7 viewed along lines VIII—VIII and IX—IX respectively, of FIG. 7.

With initial reference to FIGS. 1–3, a portion of a flexible material layer 100 for receiving an array or matrix thereon for measuring the dynamic gait analysis of a patient is shown in FIG. 1 according to the preferred embodiment of the present invention. FIGS. 2 and 3 illustrate cross sections of the first flexible material layer 100 of FIG. 1 viewed along lines II—II and III respectively.

Flexible material layer 100 has inner and outer sides 102, 104 respectively, and is advantageously fabricated from Mylar or Kapton. The manufacture of the portable sensing apparatus involves, first silk-screening traces or strips of an electrode fabricated from a conductive material, such as silver or copper on to inner side 102 of flexible material 100, to form primary conductive traces such as those indicated as 106, 108, and 110. Each primary conductive trace 106, 108, and 110 begins with a connecting primary finger 112, 114, 116, and splits along the way to create multiple primary conductive sensor contact region as indicated at regions 106A–C, 108A–C, and 110A–C on the end of primary conductive traces 106, 108, 110 opposite connecting primary fingers 112, 114, 116. It is understood that although the figures illustrate only three primary conductive traces 106, 108, 110, the flexible material may comprise numerous conductive traces as part of a much larger matrix. It is understood that the invention is not limited by the number of primary conductive traces illustrated in the figures. For simplification in explanation, the invention will be discussed in more detail with reference to electrode 110 which extends from connecting primary finger 116 as illustrated in FIG. 1. It is understood that the explanation of the present invention with reference to electrode 110 is equally applicable to all the other electrodes on the matrix.

Next, as illustrated in FIG. 4, primary conductive sensor contact regions indicated at 110A, 110B, 110C and a portion of the primary conductive trace 110 are preferably covered with a continuous thin layer of pressure responsive resistive material 118 to form the primary resistive trace 124, and the corresponding primary resistive sensor contact regions such as those indicated at 124A, 124B and 124C. As illustrated in FIG. 4, each of these primary resistive sensor contact regions, such as indicated by 124A, 124B, 124C, define multiple cells 150 arranged in a matrix over the area of first flexible material layer 100. As shown, connecting primary finger 116 is not covered. The pressure responsive resistive material 118 is advantageously a material as described in U.S. Pat. No. 3,806,471 and incorporated herein by reference, or one of many others which are commercially available, such as material no. 4430 manufactured by Chomerics and material no. 4423S manufactured by Acheson Colloids. FIGS. 5 and 6 provide side views of inner side 102 of flexible material 100 having primary conductive sensor contact regions 110A, 110B and 110C and a portion of primary conductive trace 110 fully covered with a continuous thin layer of pressure responsive resistive material 118, and viewed along lines V—V and VI—VI, respectively.

Figure 9:
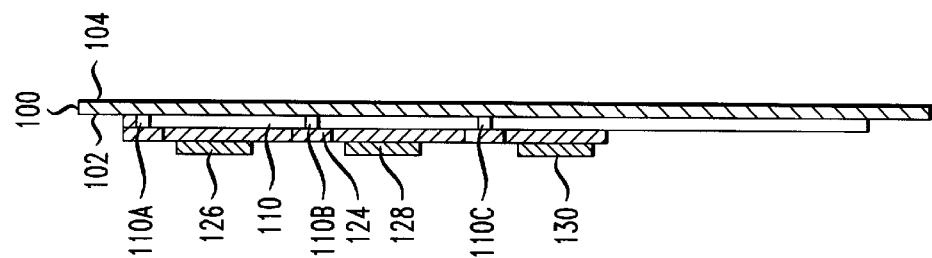
Figure 7:
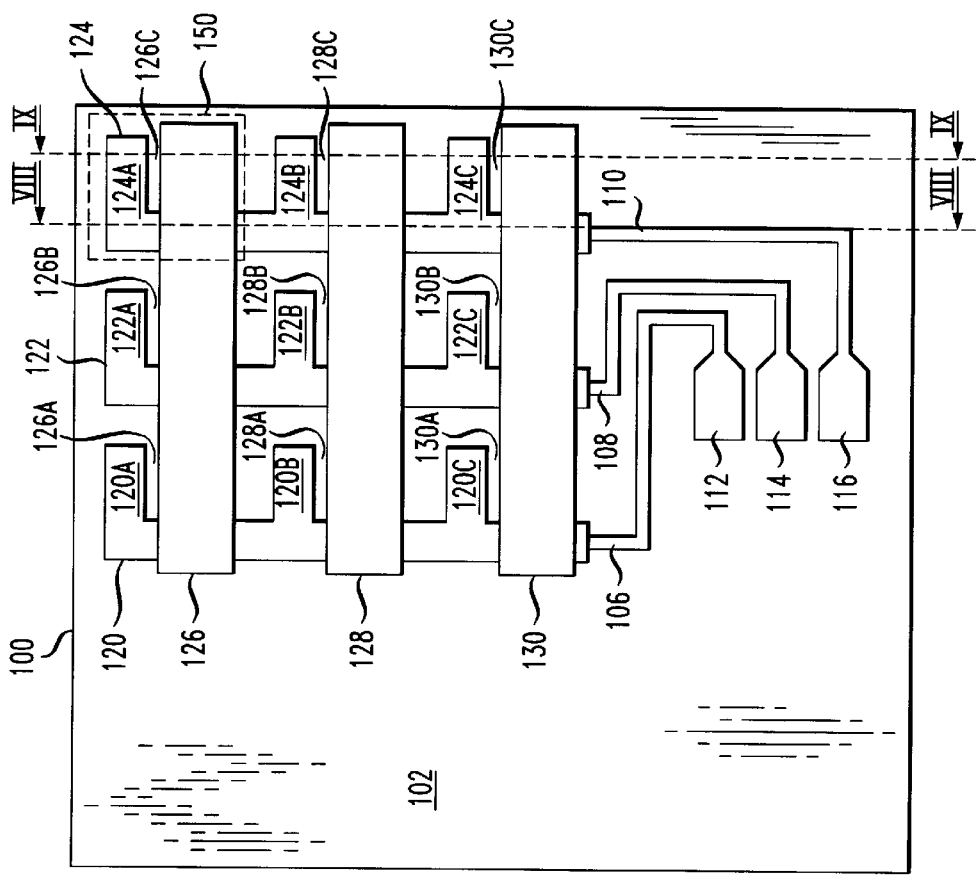
FIG. 7 illustrates a plan view of a portion of a first flexible material layer as illustrated in FIG. 4 according to one embodiment of the present invention and including strips of an insulating acrylic material silk-screened at an angle crossing each primary resistive trace.

As illustrated in FIG. 7, traces or strips of insulating acrylic material, such as material no. ML25198 manufactured by Acheson Colloids and indicated as 126, 128, 130, are then silk-screened at an angle crossing primary resistive trace 124 (as well as the other primary resistive traces 120, 122 as shown in FIG. 7) and forming gaps, such as 126C, 128C, and 130C, between the primary resistive sensor contact regions 124A, 124B, 124C of primary resistive trace 124 and the insulating traces 126, 128, 130. The application of the insulating acrylic material strips 126, 128, 130 upon primary resistive trace 124 positioned on inner side 102 of flexible material 100 can be seen in FIGS. 8 and 9 which are viewed along lines VIII—VIII and IX—IX of FIG. 7 respectively.

Figure 11:
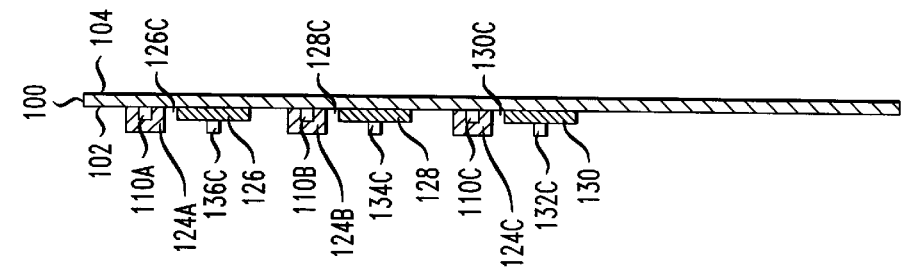
FIGS. 11 and 12 illustrate cross sections of the first flexible material layer of FIG. 10 viewed along lines XI—XI and XII—XII respectively, of FIG. 10.
Figure 12:
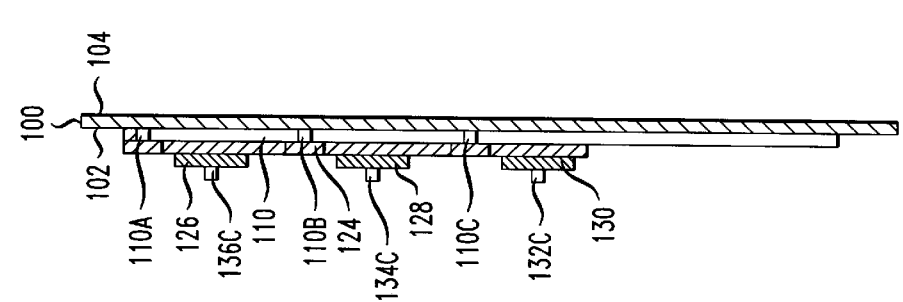
Figure 10:
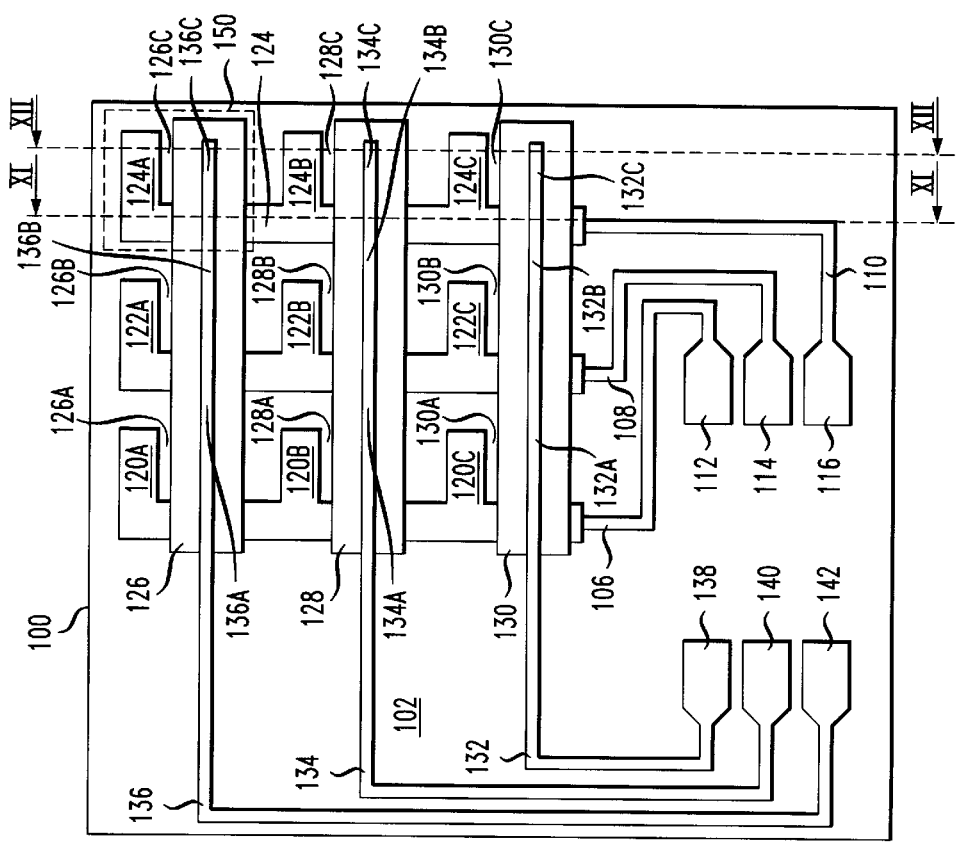
FIG. 10 illustrates a plan view of a portion of a first flexible material layer as illustrated in FIG. 7 according to one embodiment of the present invention and including secondary conductive traces silk-screened on top of the insulating acrylic material strips.

Secondary conductive traces 132, 134, 136 are then silk-screened on top of the strips of insulating acrylic material such as 126, 128, 130, as shown in FIG. 10, and which can be viewed from the side in FIGS. 11 and 12. Secondary conductive traces 132, 134, 136 are advantageously fabricated from strips of silver or copper similar to the primary conductive traces 106, 108, 110. Each secondary conductive trace 132, 134, 136 emanates from a connecting primary finger 138, 140, 142 at one end, and which comprise a plurality of secondary conductive sensor contact regions 132A–C, 134A–C and 136A–C on the opposite end. Connecting primary fingers 138, 140, 142 are aligned opposite connecting primary fingers 112, 114, 116 from which primary conductive traces 106, 108, 110 emanate.

As illustrated in FIG. 13, each secondary conductive trace 132, 134, 136 is then covered lengthwise with a continuous thin layer of pressure responsive resistive material to form secondary resistive traces 148, 146, 144 respectively. The continuous thin layer of pressure responsive resistive material used to form the secondary resistive traces 144, 146, 148 may be identical to the pressure responsive resistive material 118 which is used to form primary resistive traces 120, 122, 124 as shown in FIGS. 4–6. As further illustrated in FIG. 13, the layer of pressure responsive resistive material used to form the secondary resistive traces 144, 146, 148 does not, however, cover the width of each insulating acrylic material strip 126, 128, 130. Additionally, connecting primary fingers 138, 140, 142 are not covered.

With continued reference to FIG. 13 and to FIGS. 14 and 15, each secondary resistive trace 144, 146 and 148 defines a plurality of secondary resistive sensor contact regions such as indicated at 144C, 146C, and 148C. Secondary resistive sensor contact regions 144C, 146C, 148C are separated from their corresponding primary resistive sensor contact regions indicated at 124A, 124B and 124C. As shown in FIG. 15, primary resistive sensor contact region 124A with primary conductive sensor contact region 110A is formed at a height different from the height of secondary resistive sensor contact region 144C. Secondary resistive sensor contact region 144C is higher than primary resistive sensor contact region 124A as a result of the height of insulating acrylic material strip 126 and secondary conductive trace 136C.

Figure 17:
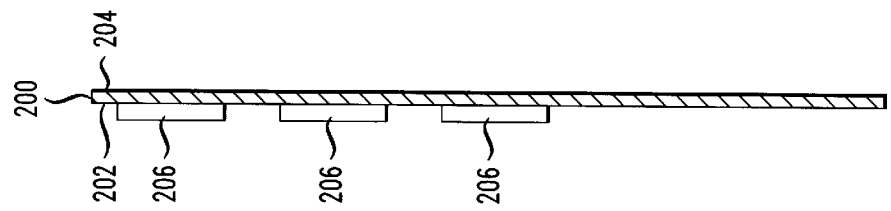
FIG. 17 illustrates a cross section of the second flexible material layer of FIG. 16 viewed along line XVII—XVII of FIG. 16.
Figure 16:
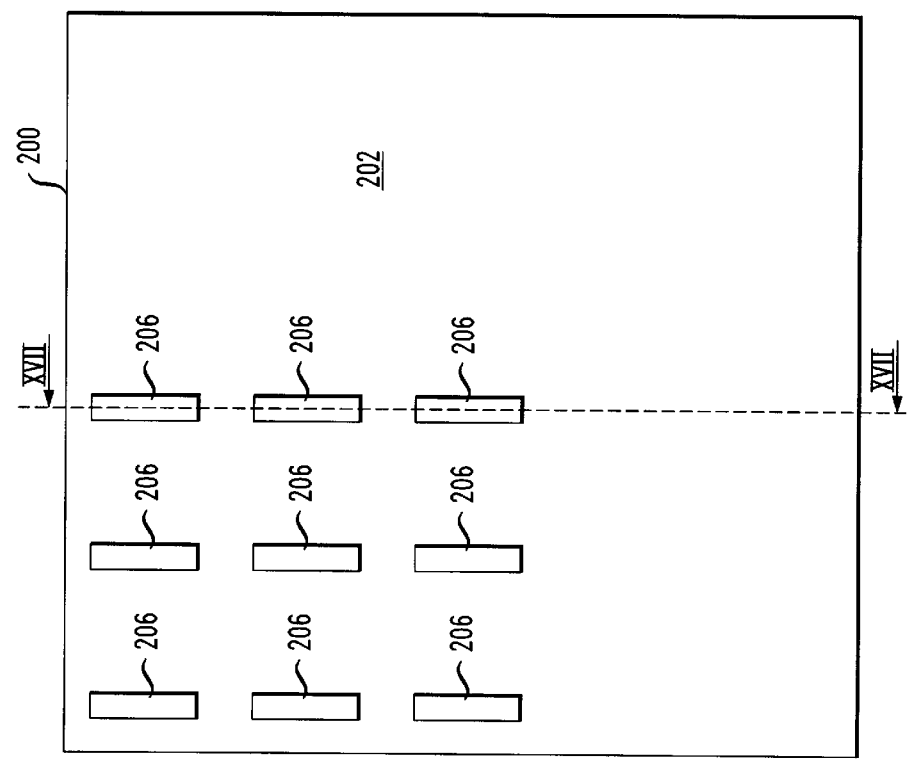
FIG. 16 illustrates a plan view of a portion of a second flexible material layer having traces of a conductive material silk screened therein to form conductive rocking bridge surfaces.

Using a second piece of a flexible material 200 such as Mylar or Kapton, having an inner side 202 and an outer side 204, bridge conductive material traces or strips 206 of silver or copper which are advantageously rectangular in shape, are silk-screened on inner side 202, of second flexible material 200 as illustrated in FIG. 16 and shown from the side in FIG. 17. Bridge conductive material traces 206 are positioned on inner side 202 of second flexible material 200 in such a way that when inner surface 202 of second flexible material 200 securably overlays inner surface 102 of first flexible material 100, the bridge conductive material traces 206 will couple the primary resistive sensor contact regions such as those indicated at 124A, 124B and 124C to the secondary resistive sensor contact regions such as those indicated at 144C, 146C, and 148C respectively.

Next, each bridge conductive material trace 206 is fully covered with a thin layer of pressure responsive resistive material to form bridge contact regions 208, as seen in FIGS. 18 and 19. The pressure responsive resistive material may be the same material used to form the secondary resistive traces 144, 146, 148, shown in FIG. 13, and the pressure responsive resistive material 118 used to form primary resistive traces 120, 122, 124 shown in FIGS. 4–6, and may have similar or different pressure/resistance properties.

After each bridge conductive material trace 206 has been fully covered with pressure responsive resistive material to form bridge contact regions 208, a rocker member 212 is silk-screened across each bridge contact region 208 as illustrated in FIG. 20. Rocker member 212 is advantageously a piece of insulating material having a printable coating and which is typically ultra violet curable with good flexibility properties. It is essential that rocker member 212 be more rigid and less resilient than its surrounding material. An exemplary rocker member 212 may be made of insulating material No. ML25198 manufactured by Acheson Colloids. As shown in FIG. 21, the total height of rocker member 212 which extends upward from inner side 202 of second flexible material 200 can be varied by adjusting the height of rocker member 212, the height of the pressure responsive resistive material 208 and/or the height of bridge conductive material trace 206. In the preferred embodiment, the height of rocker member 212 is preferably the same or greater than the height of secondary resistive sensor contact region 144C as more clearly illustrated in FIG. 24.

Inner side 102 of first flexible material 100 and inner side 202 of second flexible material are brought together, overlaid upon each other and secured using an adhesive as illustrated in FIG. 22, and seen from the side in FIG. 23 when viewed along line XXIII—XXIII of FIG. 22, to define a sensor array or matrix 300 comprising a plurality of conductive cells 150 defining a circuit. As shown in FIG. 24, when inner sides 102, 202 of first and second flexible materials are brought together and secured to one another, rocker members 212 are positioned so as to fit between the gaps such as indicated at 126C, 128C, and 130C. A load exerted on outer surface 104 of first flexible material 100 over primary resistive sensor contact region 124A results in contact with one end of bridge contact region 208 on inner side 202 of second flexible material 200 at the point indicated by X. When the load is sufficiently large, the resistance of primary resistive sensor contact region 124A and the resistance of portion X of bridge contact region 208 becomes sufficiently small such that an electrical conduction can be established between primary conductive sensor contact region 110A and bridge conductive material trace 206.

Similarly, a load exerted on over secondary resistive sensor contact region 144C results in contact with bridge contact region 208 on inner side 202 of second flexible material 200 at the point indicated by Y. When the load is sufficiently large, the resistance of secondary resistive sensor contact region 144C and the resistance of portion Y of bridge contact region 208 becomes sufficiently small such that an electrical conduction can be established between secondary conductive sensor contact region 136C and bridge conductive material trace 206.

However, if one load acts simultaneously over primary and secondary sensor contact regions 110A, 136C, then an electrical conduction can be established between primary conductive sensor contact region 110A and secondary conductive sensor contact region 136C through bridge conductive material trace 206. This follows because the pressure resistive material on the surfaces of secondary resistive sensor contact region 144C and bridge contact region 208 exhibits a low resistance between the two surfaces upon contact proportional to the load exerted between the two surfaces. Likewise, the pressure resistive material on surfaces of primary resistive sensor contact region 124A and bridge contact region 208 exhibits a low resistance between the two surfaces upon contact proportional to the force exerted between the two surfaces. As such, the amount of current present in secondary conductive sensor contact region 136C is proportional to the exerted load. Bridge contact region 208 ensures that all four surfaces, i.e. the upper surfaces of primary resistive sensor contact region 124A, bridge contact region 208 at point X, bridge contact region 208 at point Y and secondary resistive sensor contact region 144C, must be in contact for current to flow from primary conductive trace 110A conductor to secondary conductive sensor contact region 136C. Furthermore, rocker member 212 causes the primary and secondary resistive sensor contact regions 124A, 144C to quickly revert to their original non-conductive state as soon as the load is removed.

An alternative embodiment of the invention in accordance with the principles described hereinabove is illustrated in FIG. 25. Similar to the arrangement illustrated in FIG. 24, the pressure sensing arrangement illustrated in FIG. 25 comprises first flexible backing material 100. Layers of primary conductive traces 352, 354 and 356 are disposed over flexible backing material 100, to form driving electrodes for conducting electric currents. As illustrated in FIG. 25, each primary conductive trace 352, 354, 356 is longitudinally extended to form a driving electrode row that terminates with primary fingers 384, 382, 380, respectively. Over a portion of each conductive trace 352, 354, 356, a thin layer of pressure responsive resistive material is disposed to form primary resistive traces, 358, 360 and 362, respectively.

A second flexible backing material 200 is employed to receive layers of secondary conductive traces 368, 370 and 372, to form sensing electrodes for conducting electric currents. As illustrated in FIG. 25, each secondary conductive trace 368, 370, 372, is longitudinally extended to form a sensing electrode column that terminates with a secondary finger such as 378, 376, 374, respectively. Over a specified portion of each secondary conductive trace 368, 370, 372, a thin layer of pressure responsive resistive material is disposed to form secondary resistive traces 344.

A rocker member 212 is disposed over each secondary resistive trace as illustrated in FIG. 25. It is noted that rocker member 212 is disposed in the form of a horizontal strip over secondary resistive traces 344, although the invention is not limited in scope in that respect. For example, rocker member 212 may employ a width such that it only substantially covers each secondary resistive trace 344. As previously described, each rocker member 212 is made of a material that is more rigid than the pressure responsive resistive materials employed to form the arrangement in accordance with the present invention. Furthermore, the height of each rocker member 212 is preferably substantially the same or larger than the height of the primary resistive traces such as 358, 360 and 362, however, the invention is not limited in scope in that respect.

The two layers 100 and 200 are securably disposed over each other by an adhesive to form the arrangement illustrated in FIG. 25a. Each primary conductive trace 352, 354, 356 in combination with a corresponding secondary conductive trace 368, 370, 372, and intermediate primary resistive traces 358, 360, 362 and secondary resistive trace 344 along with rocker element 212, form a primary resistive sensor contact region such as 124A, as illustrated in FIGS. 25 and 25a, although the invention is not limited in scope in that respect. For example, a primary resistive sensor contact region may be formed by a primary and secondary conductive trace separated by an intermediate pressure responsive resistive material and a rocker member that is extended within the gap defined by the primary and secondary conductive traces and the intermediate pressure responsive resistive material.

During operation, when flexible layers 100 and 200 are not exposed to a load, each primary resistive sensor contact region exhibits a substantially high resistance or impedance due to the use of pressure responsive resistive materials that form primary and secondary resistive traces. When a load is exerted on either or both flexible backing layers 100 and 200, the resistance of each pressure responsive resistive material decreases until such time that a conductive contact is established between a driving and sensing electrode at the region where the load has been exerted. When the load is removed, rocker element 212 causes the pressure responsive resistive material to quickly revert back to their original state prior to the exertion of the load.

Because rocker member 212 is made of a material that is more rigid than the pressure responsive resistive material, the time that it takes to revert to the original state is substantially shorter than conventional sensors. It is noted that although the height of rocker member 212 is illustrated to be the same as primary resistive traces, such as 358, 360 and 362, the invention is not limited in scope in that respect. For example, the height of the rocker members may be shorter than the primary resistive traces, provided that a pressure exerted on a primary resistive trace adjacent to the rocker member, causes the primary resistive trace be compressed to a height that is smaller than the height of the rocker member. In that event, the rocker member is still beneficial, because its height is larger than the height of a compressed primary resistive trace adjacent to it. When the load is removed the rocker element helps the primary resistive traces to revert back to their original state more rapidly.

Since the primary resistive traces in accordance with the present invention revert back to their original state remarkably quicker than conventional sensors, it is possible to employ thicker flexible backing materials. This allows the user of the apparatus of the present invention to fold the backing material for easier transportation, without deforming the apparatus after repeated folding and unfolding.

Figure 26:
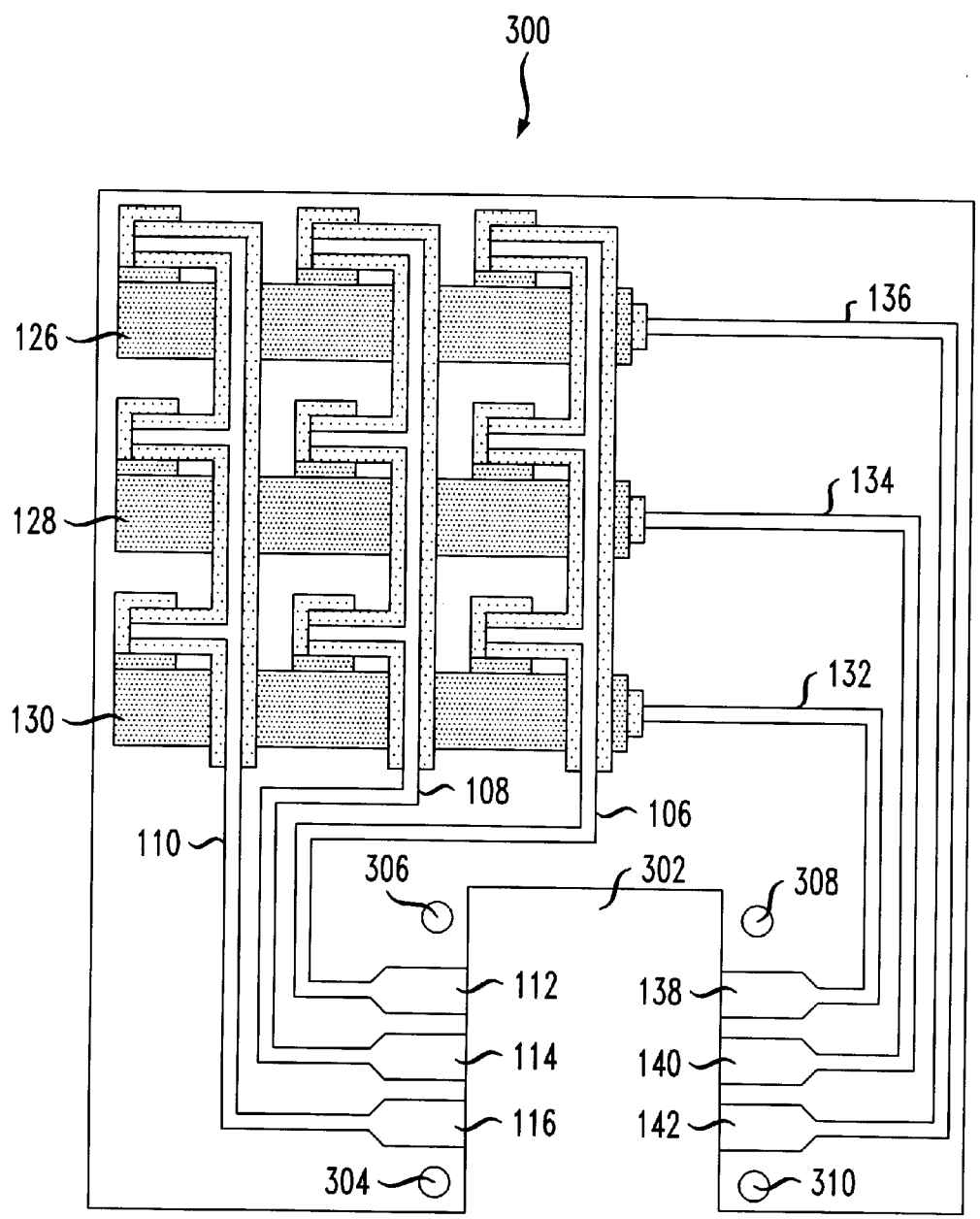
FIG. 26 is a plan view of the sensor array of FIG. 22 according to one embodiment of the present invention and having a portion of the sensor array cut away.

After inner sides 102, 202 of first and second flexible materials 100, 200 respectively are brought together and secured, a portion of the combined flexible material layers is cut away, as indicated at 302, in the region of the sensor array between connecting primary fingers 112, 114, 116 and 138, 140, 142 as illustrated in FIG. 26. Additionally, mounting holes 304, 306, 308 and 310 are punched about the boundary of cutout portion indicated at 302 for receiving screws 402 (shown in FIGS. 27 and 28).

Next, a circuit board 400 containing the electronics having attached conductive fingers 404, 406, 408, 410, 412, 414 is inserted between the first (top)flexible material layer 100 and second (bottom) flexible material layer 200. Circuit board 400 generally includes a power source signal (not shown) for providing a current flow through sensor array 300. A plurality of sensors (not shown) may be positioned on circuit board 400 opposite the electrical source such that the sensors detect a signal provided when the circuits on sensor array 300 have been closed as a result of a force exerted on outer side 102 of first flexible material 100. Circuit board 400 is positioned such that connecting fingers 404, 406, 408 on one side of circuit board 400 are aligned with connecting primary fingers 112, 114, 116 on sensor array 300, and connecting fingers 410, 412, 414 on the opposite side of circuit board 400 are aligned with connecting primary fingers 138, 140, 142 on sensor array 300 as illustrated in FIG. 27. Circuit board 400 is further provided with mounting holes which correspond to mounting holes 304, 306, 308, 310 in sensor array 300 for receiving screws therein. A gasket 420 (shown in FIG. 28) is then placed upon the placed on periphery of the upper surface of circuit board 400 as shown in FIG. 28 and a metal bar 418 is then disposed upon gasket 420 to receive screws 402 to facilitate securement of circuit board 400 with sensor array 300.

Figure 29:
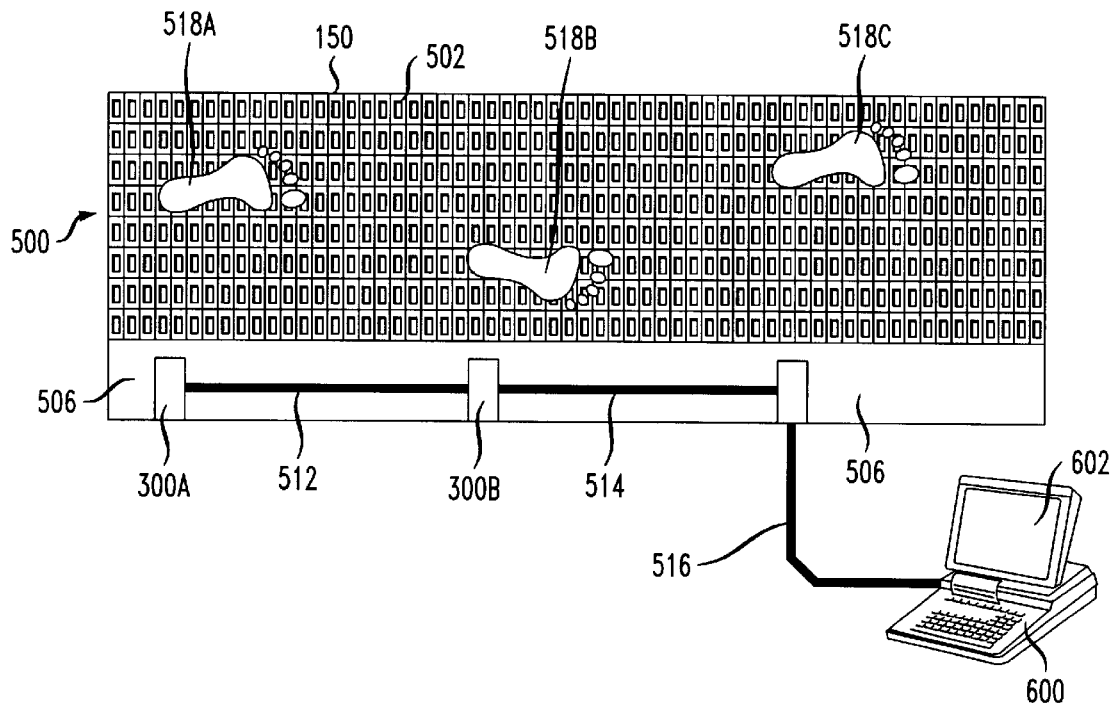
FIG. 29 is a plan view of a walkway comprised of multiple sensor arrays according to one embodiment of the present invention connected to a personal computer.

The attachment of circuit board 400 and its electronics to sensor array 300 comprises walkway 500, as illustrated in FIG. 29, and having top surface 502 and a bottom surface 504, for recording the dynamic gait analysis of a patient. Walkway 500 is comprised of numerous sensor arrays 300A, 300B, 300C comprised of a numerous cells 150 arranged in a matrix. Sensor arrays 300A, 300B, 300C are advantageously arranged in series as shown in FIG. 29. As illustrated in FIG. 28, walkway 500 is provided with a self-adhesive vinyl flexible material 506 applied on top surface 502 and a self adhesive open cell rubber material cover 508 applied on bottom surface 504. The open cell rubber material from which 508 bottom surface 504 is advantageous since it permits rocker member 212 to be depressed into the rubber so as to make contact with bottom surface 504 so that a current is generated. Open cell rubber material cover 508 also aids in protecting walkway 500 when it is rolled for storage or transport. Vinyl flexible material 506 applied on top surface also protects walkway 500 and permits easy cleaning and disinfection of walkway 500 after use. As illustrated in FIG. 28, a cover 510 is placed over the electronics of circuit board 400 of each array 300.

With continued reference to FIG. 29, a cable 512 connects the electronics of the sensor arrays 300A to the electronics of the sensor array 300B. A second cable 514 connects the electronics of sensor array 300B to the sensor array 300C and so on. It is understood that a single cable may be used to connect the sensor arrays rather than a single cable connected between consecutive sensor arrays. A third cable connects the electronics of sensor array 300C to a personal computer or microprocessor 600 having a video monitor 602, and which is loaded with a software program utilized for reading, recording and analyzing the gait of a patient.

Figure 30:
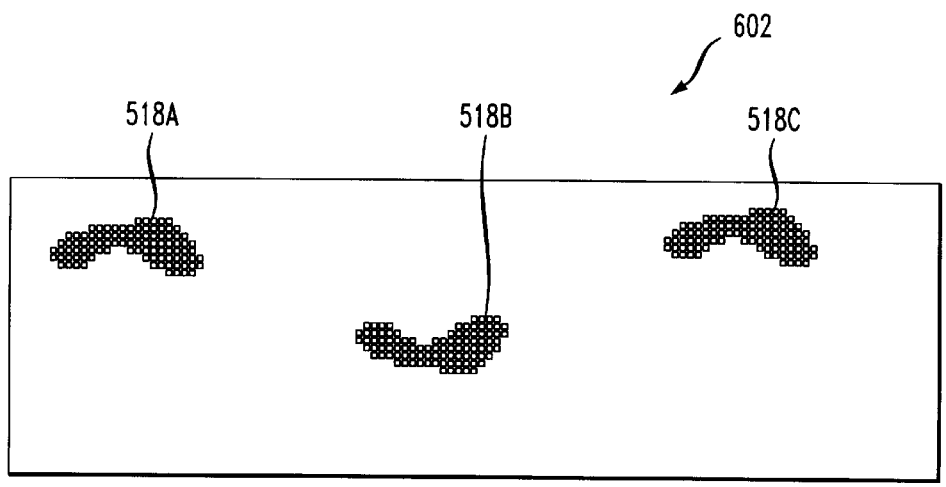
FIG. 30 is a diagrammatic view of footprints upon the walkway according to one embodiment of the present invention as the footprints would appear on a video monitor of the personal computer illustrated in FIG. 29.

In use, walkway 500 is laid upon a flat surface and the personal computer 600 is activated. Once it is ascertained that computer 600 is running properly and that first, second and third cables 512, 514, 516 are tightly connected, a person is instructed to step upon walkway 500 and walk across walkway 500 as instructed by a medical professional or physical therapist. The placement of the persons feet 520A, 520B, 520C upon walkway 500 exert pressure upon the sensor arrays 300A, 300B, 300C such that circuits are closed wherein a current is caused to flow from a primary conductive trace such as indicated by 110A in FIG. 25 across the resistive materials of the primary resistive sensor contacts, e.g. 124A, on first flexible material layer 100 and being received at a primary conductive sensor contact such as 136C. The flow of current in sensor arrays 300A, 300B, 300C is converted to an electronic signal and communicated to personal computer 500 via first, second and third cables 512, 514 and 516. Software loaded within computer 600 stores and displays the persons feet position 518A, 518B, 518C. FIG. 30 illustrates a representation of the gait of the person walking upon walkway 500 as shown in FIG. 29. The software loaded in computer 600 is then capable of reading, recording, and analyzing according to one or more predetermined parameters, the gait of the person walking upon walkway 500.

The present invention provide medical professionals and health care practitioners with valuable information about the geometry of the patient's footprints as a function of time, the relative arrangement of the footprints as a function of time and the relative strength of pressure as a function of time. Furthermore, the present invention yields information not only to the force exerted, but also the locations where the force is exerted and the position of such locations in relation to one another and as a function of time.

Thus, while there have been shown and described and pointed out fundamental novel features of the invention as applied to preferred embodiments thereof, it will be understood that various omissions and substitutions and changes in the form and details of the disclosed invention may be made by those skilled in the art without departing from the spirit of the invention. It is the intention, therefore, to be limited only as indicated by the scope of the claims appended hereto.

It is to be understood that the drawings are not necessarily drawn to scale, but that they are merely conceptual in nature.

We claim:

1. A pressure sensing array for measuring forces applied thereto, comprising:
    a first plurality of electrodes attached to and supported by a thin, flexible backing sheet to provide a set of current driving electrodes, said first plurality of current driving electrodes at least partially covered by a pressure responsive resistive material;
    a second plurality of electrodes disposed in an insulating arrangement positioned on said first plurality of electrodes to provide a set of current sensing electrodes; and
    a third plurality of bridge contacts having opposite end portions, each of said bridge contacts disposed above a corresponding one of said current sensing and current driving electrodes wherein at least one end portion of said bridge contacts is positioned in a non-conductive arrangement relative to said current driving and current sensing electrodes, such that upon sensing a pressure on both said opposite end portions of one of said bridge contacts, an electrical conduction is provided between one of said current driving and current sensing electrodes corresponding to said bridge contact.

2. The apparatus as recited in claim 1, wherein said second plurality of current sensing electrodes are disposed at a specified angle over said first plurality of current driving electrodes and said pressure responsive resistive material to form primary contact regions.

3. The apparatus as recited in claim 1, further comprising a rocker member disposed upon each of said bridge electrodes and positioned between said first and said second plurality of electrodes.

4. The apparatus as recited in claim 3, wherein said rocker member is disposed substantially adjacent to at least one of said primary contact regions, said rocker member being fabricated from a material that is more rigid than the pressure responsive resistive material.

5. The apparatus as recited in claim 1, wherein each of said first plurality of current driving electrodes have a first end and a second end, said first end comprising connecting primary fingers, said second end extending upon said first thin, flexible backing sheet and dividing into a plurality of primary sensor contact regions positioned along said first plurality of current driving electrodes.

6. The apparatus as recited in claim 1, wherein each of said second plurality of current sensing electrodes have a first end and a second end, said first end comprising connecting primary fingers arranged on said first thin, flexible backing opposite said connecting primary fingers of a corresponding one of said first plurality of current driving electrodes, said second end extending upon said first thin, flexible backing sheet and dividing into a plurality of secondary sensor contact regions along a corresponding one of said second plurality of current sensing electrodes.

7. The apparatus as recited in claim 4, wherein an insulating arrangement is disposed on said first plurality of current driving electrodes and is positioned across said first plurality of current driving electrodes to define gaps between said second plurality of current sensing electrodes and said insulating arrangement.

8. The apparatus as recited in claim 7, wherein said rocker members are positioned on said bridge electrodes so as to extend within said gaps when said first and second thin, flexible backing sheets are secured to one another.

9. The apparatus as recited in claim 8, wherein said first and second thin, flexible backing sheets are secured to one another using an adhesive.

10. The apparatus as recited in claim 4, wherein said rocker members are of a height such that at least one of said opposite end portions of said bridge contacts are spaced from said first and second plurality of current driving and sensing electrodes such that a pressure exerted on both end portions of said bridge contact causes a current flow from a corresponding one of said first plurality of current driving electrodes to a corresponding one of said second plurality of current sensing electrodes.

11. The apparatus as recited in claim 5, further comprising a circuit board having a power source and plurality of sensors, said circuit board attached between said first and second thin, flexible backing sheets and positioned between said oppositely arranged primary connecting fingers of said first plurality of current driving electrodes and said second plurality of current sensing electrodes.

12. The apparatus as recited in claim 1, wherein said first plurality of current driving electrodes and said second plurality of current sensing electrodes are fabricated from strips of silver.

13. The apparatus as recited in claim 1, wherein said first plurality of current driving electrodes and said second plurality of current sensing electrodes are fabricated from strips copper.

14. The apparatus as recited in claim 10, wherein said first and second thin, flexible backing sheets are fabricated from Mylar.

15. The apparatus as recited in claim 10, wherein said first and second thin, flexible backing sheets are fabricated from Kapton.

16. A pressure sensing array for measuring loads applied thereto, comprising:
    a first plurality of current driven electrodes attached to a flexible backing sheet said first plurality of electrodes at least partially covered by a pressure responsive resistive material;
    a second plurality of current sensing electrodes disposed at a specified angle over said first plurality of electrodes and said pressure responsive resistive material to form primary contact regions, said second plurality of electrodes attached to a second flexible backing sheet, such that a gap is formed between said first and second flexible backing sheets; and
    a rocker member disposed substantially adjacent to at least one of said primary contact regions, wherein said rocker member is made of a material that is more rigid than the pressure responsive resistive material.

17. The apparatus as recited in claim 16, wherein said current driving and current sensing electrodes are perpendicular to each other.

18. The apparatus as recited in claim 16, wherein height of said rocker is the same as the height of said pressure responsive resistive material.

19. The apparatus as recited in claim 16, wherein height of said rocker is larger than said pressure responsive resistive material.

20. The apparatus as recited in claim 16, wherein height of rocker is smaller than the height of pressure responsive resistive material provided that a pressure exerted on said flexible backing sheet causes the pressure responsive resistive material be compressed to a height that is smaller than the height of said rocker member.

21. A method of manufacturing a pressure sensing array for measuring forces applied thereto, which comprises the steps of:

disposing a first plurality of electrodes upon a first thin, flexible backing sheet;

disposing a second plurality of electrodes in an insulating arrangement positioned on said first plurality of electrodes; and disposing a third plurality of bridge contacts having opposite end portions, each of said bridge contacts disposed above a corresponding one of said current sensing and current driving electrodes wherein at least one end portion of said bridge contacts is positioned in a non-conductive arrangement relative to said current driving and current sensing electrodes, such that upon sensing a pressure on both said opposite end portions of one of said bridge contacts, an electrical conduction is provided between one of said current driving and current sensing electrodes corresponding to said bridge contact.

22. The method as recited in claim 21, wherein the step of disposing said electrodes on said first thin, flexible backing layer are disposed thereon via a silk-screening process.

23. The method as recited in claim 21, wherein said step of disposing said first plurality of current driving electrodes on said first thin, flexible backing sheet further comprises the step of covering said first plurality of current driving electrodes with a layer of resistive material.

24. The method as recited in claim 23, wherein said resistive material is a pressure responsive resistive material.

25. The method as recited in claim 21, further comprising the step of disposing strips of adhesive material on said bridge electrodes for securing a second thin, flexible backing sheet upon said first thin, flexible backing sheet.

26. The method as recited in claim 25, further comprising the step of cutting out a portion of said first and second thin, flexible backing sheets and securing a circuit board therebetween for providing and receiving electrical signals across said pressure sensing array.

* * * * *